United States Patent [19]

Lorenz

[11] Patent Number: 5,117,686
[45] Date of Patent: Jun. 2, 1992

[54] SCANNING HEAD POSITION SENSING FOR WEB CHARACTERISTIC MEASURING SYSTEM

[75] Inventor: Ralph S. Lorenz, Columbus, Ohio

[73] Assignee: ABB Process Automation Inc., Columbus, Ohio

[21] Appl. No.: 687,332

[22] Filed: Apr. 18, 1991

[51] Int. Cl.⁵ .................... G01L 5/04; G01N 27/72; G01R 33/00
[52] U.S. Cl. ............................. 73/159; 73/37.6; 324/225
[58] Field of Search ........... 73/37.5, 37.6, 37.7, 73/37.8, 37.9, 159; 250/358.1, 359.1, 360.1; 324/207.17, 207.19, 225, 226, 227, 229

[56] References Cited

U.S. PATENT DOCUMENTS

| | | |
|---|---|---|
| 3,243,992 | 4/1966 | Woods . |
| 3,703,097 | 11/1972 | Kilpatrich et al. ............ 73/159 |
| 3,714,558 | 1/1973 | Swanepoel ............ 324/225 |
| 3,757,122 | 9/1973 | Bossen et al. . |
| 3,926,053 | 12/1975 | Schurrer et al. . |
| 4,160,204 | 7/1979 | Holmgren et al. . |
| 4,276,480 | 6/1981 | Watson . |
| 4,404,634 | 9/1983 | Bautz ............ 73/159 X |
| 4,453,404 | 6/1984 | Powell et al. ............ 73/159 |
| 4,678,915 | 7/1987 | Dahlquist . |
| 4,686,471 | 8/1987 | Morita et al. ............ 324/225 X |
| 4,823,082 | 4/1989 | Nasu et al. ............ 324/225 X |

Primary Examiner—William A. Cuchlinski, Jr.
Assistant Examiner—G. Bradley Bennett
Attorney, Agent, or Firm—Killworth, Gottman, Hagan & Schaeff

[57] ABSTRACT

In a scanning head position sensing method and apparatus, a plurality of distinct electromagnetic signals are transmitted from a corresponding plurality of transmitter sites surrounding a central position on one side of a web of material. The signals are transmitted through the web and are received by an electromagnetic energy sensor on the opposite side of the web of material. The electromagnetic energy sensor is positioned to receive approximately equal signal energies from all the transmitters when the energy sensor is positioned substantially opposite to the central position across the web. The transmitters and the sensor are fixedly positioned relative to the first and second sensor heads such that the relative positioning of the heads is determined by combining the signals with one another. Pairs of transmitters are provided at two locations along each of two axes which cross on the central position such that the positioning of the sensor heads can be determined for machine and cross directions and also along the axes. Preferably, the axes are oriented at 45° and 135° relative to the machine direction such that information regarding the positioning of the sensor heads can be determined in the machine direction, the cross direction and along 45° and 135° directions relative to the machine direction.

19 Claims, 3 Drawing Sheets

SCANNING HEAD POSITION SENSING FOR WEB CHARACTERISTIC MEASURING SYSTEM

BACKGROUND OF THE INVENTION

The present invention relates generally to the measurement of various parameters or characteristics of a web of sheet material as it is being manufactured and, more particularly, to a method and apparatus for measuring the relative positions of two heads which are used to perform the measurement such that errors due to variations in the measurement head positions can be compensated.

A variety of systems are known for measuring characteristics of webs of sheet material as the webs are moving in a first machine direction in a manufacturing process. For example, first and second sensing members are often physically moved or swept in a second cross direction generally perpendicular to movement of the web with the members supported for movement on opposite sides of the web by a support frame. For determining basis weight of a paper web, the members may be a beta radiation source on one side of the web and a beta radiation sensor on the opposite side. For moisture content of a paper web, the members may be a source of infrared radiation on one side and a detector to receive infrared radiation on the opposite side.

For many measurement systems, the positioning between the two sensing members or heads can significantly affect the determination of the characteristic being measured. Such measurement effects are particularly apparent in the basis weight measurement noted above. Further, the positioning between the sensor heads can sometimes vary unpredictably such that cross direction distance variation patterns determined for a given support frame and measurement system cannot generally be relied upon.

For non-magnetic materials, a popular method for determining the positioning or relative motion between two sensor heads such that the corresponding characteristic readings can be appropriately compensated is to pass magnetic energy through the material. For example, in U.S. Pat. No. 4,678,915, magnetic energy is generated on one side of a web of material and sensed on the other side. A transmitter of the magnetic energy is fixedly positioned relative to one of the sensor heads and a primary receiver of the magnetic energy is fixedly positioned relative to the other sensor head such that the magnitude of the received magnetic energy is representative of the spacing between the two heads. Ideally, the transmitter and the receiver are axially aligned with one another. To detect and correct for inaccurate alignment, secondary receivers can be positioned adjacent to the primary receiver. One or more pairs of secondary receivers are positioned adjacent to and on opposite sides of the primary receiver with secondary receiver pairs aligned in either the machine direction or the cross direction or both.

While such known prior art position sensing arrangements improve the determinations of characteristic measurement systems which are sensitive to the relative motion of scanned sensor heads relative to one another, there is a need to provide alternatives which are potentially more accurate and have the capacity to provide additional information to operators of characteristic measurement systems.

SUMMARY OF THE INVENTION

This need is met by the scanning head position sensing method and apparatus of the present invention wherein a plurality of distinct electromagnetic signals are transmitted from a corresponding plurality of sites surrounding a central position. The transmitter sites are associated with a first sensor member or head on one side of a web of material to be monitored. The distinct electromagnetic signals are transmitted through the web and are received by an electromagnetic energy sensor associated with a second sensor member or head on the opposite side of the web of material. The electromagnetic energy sensor is positioned to receive approximately equal signal energies from all the transmitters when the energy sensor is positioned substantially opposite to the central position across the web. The relative positioning of the first and second sensor members is determined by combining the distinct electromagnetic energy signals with one another.

Since the energy sensor is substantially centrally located relative to the transmitted signals, the magnitude of the combination of all the transmitted signals is used to indicate the spacing or separation between the first and second sensor members across the web. Since the possible positioning for the first and second sensor members relative to one another is limited even for worst case variations in their positioning, the magnitude of the overall combination gives a highly accurate measurement of the separation distance.

By providing pairs of distinct signal transmissions at two locations along each of two axes which cross on the central position, the positioning of the sensor members or heads also can be determined for the machine and cross directions, the directions along the two axes, and, by well known vector techniques, the magnitude and angular displacement of one of the heads relative to the other, i.e. separation distance along any axis through the central position. Preferably, the two axes are oriented at 45° and 135° relative to the machine direction such that information regarding the positioning of the sensor members or heads can be determined readily in the machine direction, the cross direction and along 45° and 135° directions relative to the machine direction.

The present invention is for use in a system for measuring characteristics of a web of sheet material moving in a first direction by reciprocally scanning sensor means across the web in a second direction substantially perpendicular to the first direction, the sensor means including first and second members positioned on opposite sides of the web and being moved relative to one another as the result of the sensor means being scanned across the web. In accordance with one aspect of the present invention a method for determining the positioning of the first and second members relative to one another comprises: generating a plurality of distinct electromagnetic signals at a corresponding plurality of sites surrounding a central position on a first side of the web of material; receiving the plurality of distinct electromagnetic signals at a position substantially directly opposite to the central position on a second side of the web of material; and, combining the plurality of distinct electromagnetic signals to determine the positioning between the first and second members.

The distinct electromagnetic signals are preferably of different frequencies to distinguish the signals although other distinctions are possible in accordance with the present invention. The step of generating a plurality of distinct electromagnetic signals may comprise: generating signals at two points on a first axis passing through the central position, the two points on the first axis being equally spaced from and on opposite sides of the central position; and, generating signals at two points on a second axis crossing the first axis substantially at the central position, the two points on the second axis being equally spaced from and on opposite sides of the central position, the signals received from the two points on the first axis being combined with the signals received from the two points on the second axis to determine the positioning of the first and second members in the first and second directions.

The step of generating a plurality of distinct electromagnetic signals may also comprise generating signals at first and second points on a first axis passing through the central position, the first and second points being equally spaced from and on opposite sides of the central position; and, generating signals at third and fourth points on a second axis crossing the first axis substantially at the central position, the third and fourth points being equally spaced from and on opposite sides of the central position, the signals received from the first and second points being combined with the signals received from the third and fourth points to determine the positioning of the first and second members in the first and second directions.

Preferably, the first axis is oriented at approximately 45° relative to the first direction and the second axis is oriented at approximately 135° relative to the first direction, the signals received from the first and third points being subtracted from the signals received from the second and fourth points to determine relative positioning between the first and second members in the first direction. To determine relative positioning between the first and second members in the second direction, the signals received from the second and third points are subtracted from the signals received from the first and fourth points. To determine relative positioning of the first and second members along the first and second axes, the signals received from the second point are subtracted from the signals received from the first point for positioning between the first and second members along the first axis, and the signals received from the third point are subtracted from the signals received from the fourth point for positioning between the first and second members along the second axis.

In accordance with another aspect of the present invention, apparatus for determining the positioning of the first and second members relative to one another comprises a plurality of electromagnetic energy transmitters supported adjacent the first member on a first side of the web of material and surrounding a central position, the transmitters each transmitting a different frequency electromagnetic energy signal. An electromagnetic energy sensor is supported adjacent the second member on a second side of the web and substantially directly opposite to the central position for receiving signals transmitted by the transmitters. Circuit means are connected to the sensor for receiving and combining signals transmitted by the plurality of transmitters to determine the positioning between the first and second members. The plurality of electromagnetic energy transmitters may comprise first and second transmitters positioned on a first axis passing through the central position, the first and second transmitters being equally spaced from and on opposite sides of the central position, and third and fourth transmitters positioned on a second axis crossing the first axis substantially at the central position, the third and fourth transmitters being equally spaced from and on opposite sides of the central position. For this embodiment, the circuit means combines the signals received from the first and second transmitters with the signals received from the third and fourth transmitters to determine the positioning of the first and second members in the first and second directions.

Preferably, the first axis is oriented at approximately 45° relative to the first direction and the second axis is oriented at approximately 135° relative to the first direction. The circuit means combines the signals received from the transmitters by subtracting the signals received from the first and third transmitters from the signals received from the second and fourth transmitters to determine relative positioning between the first and second members in the first direction and combines the signals received from the second and third transmitters with the signals received from the first and fourth transmitters to determine relative positioning between the first and second members in the second direction. Further positioning information can be obtained by subtracting the signals received from the second transmitter from the signals received from the first transmitter to determine relative positioning between the first and second members along the first axis, and by subtracting the signals received from the third transmitter from the signals received from the fourth transmitter to determine relative positioning between the first and second members along the second axis.

It is thus an object of the present invention to provide an improved scanning head position sensing method and apparatus for determining the relative positioning of first and second sensor members or heads such that measurements performed by scanning the heads across a web of material can be compensated to account for errors introduced by varying positioning of the heads relative to one another; to provide an improved scanning head position sensing method and apparatus for determining the relative positioning of first and second sensor heads wherein a plurality of distinct electromagnetic signals are transmitted from a corresponding plurality of locations surrounding a central position and received by a signal sensor positioned on the other side of the web with the signals being combined to determine the positioning of the sensor heads relative to one another; to provide an improved scanning head position sensing method and apparatus for determining the relative positioning of first and second sensor heads wherein pairs of transmitters centered on the central position are positioned along axes passing through the central position to determine relative positioning between the sensor heads including the spacing or separation between the sensor heads as well as the positioning in the machine direction, in the cross direction and along the axes; and, to provide an improved scanning head position sensing method and apparatus for determining the relative positioning of first and second sensor heads wherein pairs of transmitters centered on the central position are positioned along axes oriented at 45° and 135° to determine relative positioning between the sensor heads including the spacing or separation between the sensor heads as well as the positioning in the machine direction, in the cross direction and along the 45° and 135° axes.

Other objects and advantages of the invention will be apparent from the following description, the accompanying drawings and the appended claims.

DETAILED DESCRIPTION OF THE INVENTION

Figure 1:
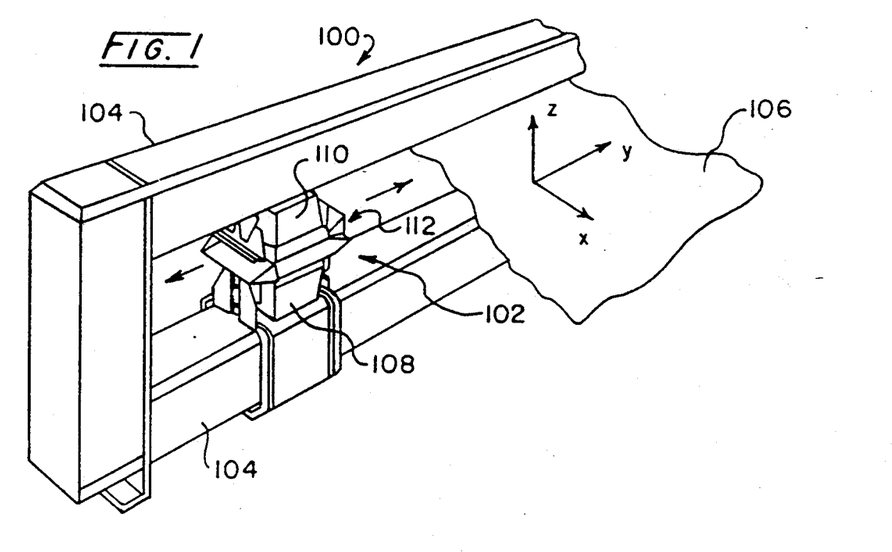
FIG. 1 is a partial perspective view of a web scanning system for which the present invention is applicable.

A partially broken-away perspective view of a web scanning system 100 for which the present invention is applicable is shown in FIG. 1. A scanner 102 is moved along a supporting frame which includes two beams 104 positioned one above a web 106 of material to be scanned and one below the web 106. The scanner 102 includes first and second members or heads 108, 110 which are moved back-and-forth along the beams 104 to scan the web 106 in the cross direction or transversely to its direction of movement during manufacture. The web 106 of material is moved in the machine or x direction as indicated by the x axis of a coordinate system shown in FIG. 1 and the cross direction is in the y direction. A gap 112 is formed between the first and second heads 108, 110 with the web 106 of material to be scanned passing through the gap 112 for the scanning operation.

Figure 2:
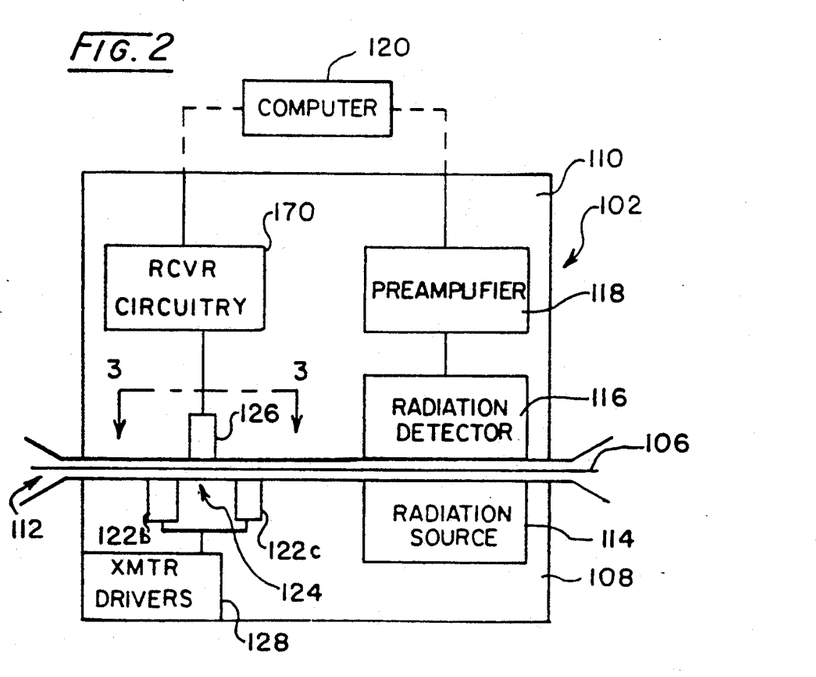
FIG. 2 is a schematic view of the web scanning apparatus of FIG. 1 including the present invention.

As shown in FIG. 2, the first and second heads 108, 110 include a radiation source 114 and a radiation detector 116. The radiation source 114 is located in the lower or first head 108 and emits beta radiation through the web 106 which in the illustration is made of paper. The beta radiation from the radiation source 114 is in the form of particles generated by a succession of events due to radioactive decay. In some applications, alpha, gamma, infrared, x-ray and other radiation may be used for the scanning operations. The radiation detector 116 is located in the upper or second head 110 and senses beta radiation which originates from the radiation source 114 and passes through the web 106. The radiation detector 116 generates an electrical signal in response to the radiation which it receives with the signal varying in correspondence with the amount of radiation received. A preamplifier 118 receives, amplifies and buffers the electrical signal from the radiation detector 116 for transmission to a computer 120 which processes and interprets the signal.

The web scanning system 100 described to this point is conventional and is used, for example, to measure the basis weight of a web of paper as it is being manufactured. By thus measuring the basis weight, adjustments can be made to more accurately control the manufacturing process and thereby improve the quality of paper being manufactured. Unfortunately, the separation of the beams 104 of the web scanning system 100 does not remain constant throughout the width of the beams 104. In fact, the separation between the beams and hence the positioning of the first and second heads 108, 110 does not repeatedly follow a separation profile as the scanner 102 is moved back-and-forth along the beams 104. For example, the separation profile is typically a function of ambient operating temperature of the web scanning system 100 which can vary considerably over time. Accordingly, it is often necessary to measure the positioning of the first and second members 108, 110 relative to one another to ensure that accurate web measurements are performed.

In accordance with the present invention, apparatus for determining the positioning of the first and second members or heads 108, 110 relative to one another comprises a plurality of electromagnetic energy transmitters 122a–122d. The transmitters 122 are supported adjacent the radiation sensor 114 of the first head 108 on a first side, the lower side as illustrated, of the web 106 of material and surround a central position 124 with each of the transmitters 122 transmitting a different frequency electromagnetic energy signal. An electromagnetic energy sensor 126 is supported adjacent the detector 116 of the second head 110 on a second side, the upper side as illustrated, of the web 106 and substantially directly opposite to the central position 124 for receiving signals transmitted by the transmitters 122. While the transmitters 122 and the sensor 126 are shown as being supported within the first and second heads 108, 110, respectively, it is apparent that they could be fixedly supported adjacent to the first and second heads 108, 110 or otherwise associated therewith and still operate in accordance with the present invention.

Figure 4:
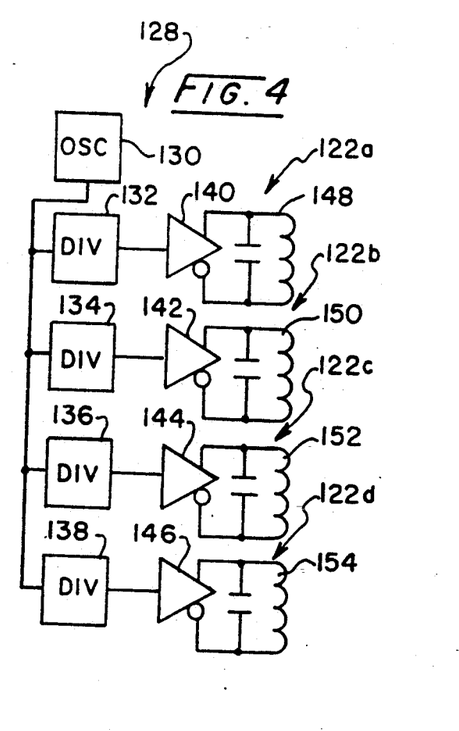
FIG. 4 is a schematic block diagram of a transmitter driver circuit for use in the present invention; and, FIG. 5 is an electrical schematic diagram of circuitry for the receiver of FIG. 3.

As best shown in FIG. 4, the transmitters 122a–122d are driven by transmitter drivers 128 schematically illustrated by a square wave oscillator 130, the output of which is divided by four divider circuits 132, 134, 136, 138 to generate drive signals for operational amplifiers 140, 142, 144, 146. The amplifiers 140, 142, 144, 146 in turn drive parallel connected inductor and capacitor pairs or tank circuits 148, 150, 152, 154 which form the transmitters 122a–122d with each transmitter 122a–122d transmitting a distinct signal, preferably a different frequency electromagnetic energy signal.

Since the signals transmitted by the transmitters 122a–122d are distinct from one another, when the signals are received by the electromagnetic energy sensor 126 the signal strengths of the signals can be used to determine the positioning of the first and second heads 108, 110 relative to one another. For example, separation of the first and second heads 108, 110 can be determined by transmitting a plurality of distinct electromagnetic signals at a corresponding plurality of sites surrounding the central position 124 on a first side of the web 106. The plurality of distinct electromagnetic signals are then received by the sensor 126 which is positioned substantially directly opposite to the central position 124 on a second or opposite side of the web 106. By combining the plurality of distinct electromagnetic signals, the spacing between the first and second members in the z direction can be determined, see FIG. 1.

While the first and second heads 108, 110 move relative to one another, such movement is restricted due to the substantial nature of the beams 104 supporting the scanner 102. Accordingly, as can be seen from FIG. 3, even though the first and second members 108, 110 move relative to one another, the sensor 126 will still be well within the box defined by corners at the positions of the transmitters 122a–122d. For this case, if the magnitude of one of the signals is reduced due to movement of the sensor 126 away from the corresponding transmitter, the signals received from the remaining transmitters will be increased collectively by an amount to substantially equal the reduction in magnitude of the one signal. In a similar manner, the signals received from two transmitters may be reduced; however, the signals received from the other two transmitters will increase collectively to substantially equal the reduction.

Figure 3:
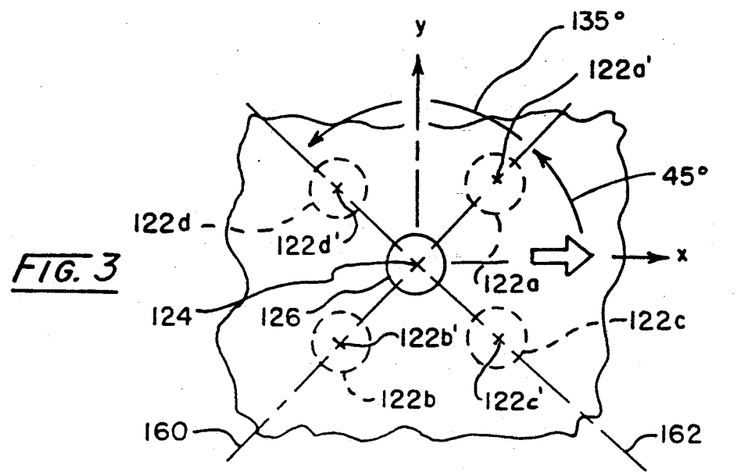
FIG. 3 is a schematic perspective view of the positioning of electromagnetic signal transmitters and a receiver substantially centered thereon.

Further, additional information regarding the positioning of the first and second heads 108, 110 relative to one another can be determined by combining the signals received by the sensor 126 from the transmitters 122a-122d. In the illustrated embodiment of the invention, signals are transmitted at two points, first and second points 122a', 122b', corresponding to the transmitters 122a, 122b on a first axis 160 passing through the central position 124. The two points on the first axis 160 are equally spaced from and on opposite sides of the central position 124. Signals are also transmitted at two points, third and fourth points 122c', 122d', corresponding to the transmitters 122c, 122d on a second axis 162 crossing the first axis 160 substantially at the central position 124. The two points on the second axis 162 being equally spaced from and on opposite sides of the central position 124. To determine the relative positioning of the first and second heads 108, 110 in the first and second directions, i.e. the x and y directions, the signals received from the two points on the first axis 160 are combined with the signals received from the two points on the second axis 162.

More specifically, the signals received from the first and third points 122a', 122c' are subtracted from the signals received from the second and fourth points 122b', 122d' to determine relative positioning between the first and second members in the first or x direction. In a corresponding manner, the signals received from the second and third points 122b', 122c' are subtracted from the signals received from the first and fourth points 122a', 122d' to determine relative positioning between the first and second heads 108, 110 in the second or y direction. It is noted that the axes 160, 162 need not be perpendicular to one another; however, in the illustrated embodiment they are with the first axis 160 being oriented at approximately 45° relative to the first or x direction and the second axis 162 being oriented at approximately 135° relative to the first or x direction.

Additional information regarding the positioning of the first and second heads 108, 110 relative to one another can be provided by determining their relative positioning along the first and second axes 160, 162. The signals received from the second point 122b' are subtracted from the signals received from the first point 122a' to determine relative positioning between the first and second heads 108, 110 along the first axis 160; and, the signals received from the third point 122c' are subtracted from the signals received from the fourth point 122d' to determine relative positioning between the first and second heads 108, 110 along the second axis 162.

While the signals received by the sensor 126 could be separated and processed directly by the computer 120, in the preferred embodiment the signals are both separated and processed by circuit means connected to the sensor 126 for receiving and combining signals transmitted by the plurality of transmitters 122a-122d to determine the spacing between the first and second heads 108, 110. It should be apparent that the positioning of the first and second heads 108, 110 can be determined along any axis through the central position 124 by the application of conventional vector techniques and that such vector position identification is contemplated for use in the present invention. Thus, if desired, x and y components can be converted to a magnitude and angle relative to a defined 0° axis, such as the x axis. In a similar manner, x, y and z components can be converted into a magnitude and solid angle if a three dimensional vector determination is desired.

Figure 5:
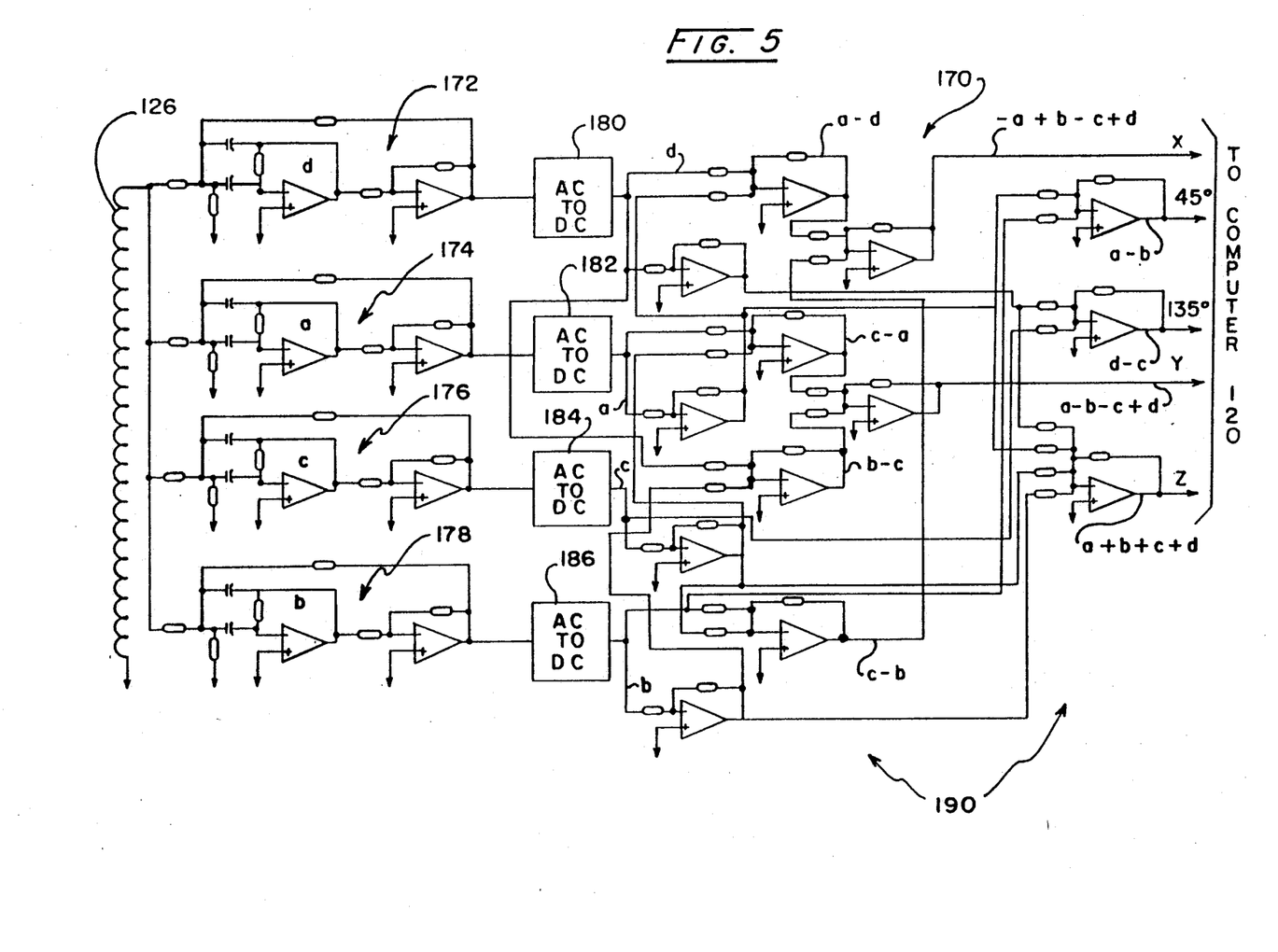

The circuit means comprises receiver circuitry 170 shown in FIGS. 2 and 5 as being connected between the sensor 126 and the computer 120. With reference to FIG. 5, the sensor 126 is shown as a pickup coil having one end connected to ground potential and the other end connected to the inputs of amplifier pairs 172, 174, 176, 178 which are connected as filter/buffering amplifiers for amplifying and passing corresponding signals to AC-to-DC converters 180, 182, 184, 186. Currently preferred signal frequencies for the transmitters 122a, 122b, 122c, 122d and the filter/buffering amplifier pairs 172, 174, 176, 178 are: 10 Khz; 10.8 Khz; 11.6 Khz; and 12.6 Khz, respectively. Appropriate values of the capacitors and resistors of the amplifier pairs 172, 174, 176, 178 can be readily determined by those skilled in the art for the currently preferred frequencies or alternate frequencies if desired. It is to be understood that the small rectangular circuit components are electrical resistors.

The output signals from the AC-to-DC converters 180, 182, 184, 186 are dc voltage levels that represent the magnitude of the corresponding frequency signals received by the sensor 126. Thus, the output of AC-to-DC converters can be combined to determine the positioning of the first and second heads 108, 110 relative to one another. The combinations of the output signals from the AC-to-DC converters 180, 182, 184, 186 are performed by the amplifiers 190 which together with appropriate resistors, again indicated by rectangular circuit elements, make up the remainder of the circuit. The combinations are as shown on FIG. 5 with the resulting positional signals being passed to the computer 120 for use in compensating the web monitoring process in accordance with well known compensation techniques which will not be described herein.

To summarize the combinations of the signals:

$$x = -a + b - c + d$$

$$45° = a - b$$

$$135° = d - c$$

$$y = a - b - c + d; \text{ and,}$$

$$z = a + b + c + d$$

where: a corresponds to the signal from the transmitter 122a (transmitted from the first point 122a'); b corresponds to the signal from the transmitter 122b (transmitted from the second point 122b'); c corresponds to the signal from the transmitter 122c (transmitted from the third point 122c'); and, d corresponds to the signal from the transmitter 122d (transmitted from the first point 122d').

Having thus described the method and apparatus of the present invention in detail and by reference to preferred embodiments thereof, it will be apparent that modifications and variations are possible without departing from the scope of the invention defined in the appended claims.

What is claimed is:

1. In a system for measuring characteristics of a web of sheet material moving in a first direction by reciprocally scanning sensor means across said web in a second direction substantially perpendicular to said first direction, said sensor means including first and second members positioned on opposite sides of said web and being moved relative to one another as the result of said sensor means being scanned across said web, a method for determining the positioning of said first and second members relative to one another comprising:

generating a plurality of distinct electromagnetic signals at a corresponding plurality of sites surrounding a central position on a first side of said web of material;

receiving said plurality of distinct electromagnetic signals at a position substantially directly opposite to said central position on a second side of said web of material; and combining said plurality of distinct electromagnetic signals to determine the positioning between said first and second members.

2. In a web measuring system, a method for determining the positioning of first and second members relative to one another as claimed in claim 1 wherein the step of combining said plurality of distinct electromagnetic signals to determine the positioning between said first and second members comprises algebraically summing said plurality of signals to determine the separation between said first and second members.

3. In a web measuring system, a method for determining the positioning of first and second members relative to one another as claimed in claim 1 wherein said distinct electromagnetic signals are of different frequencies.

4. In a web measuring system, a method for determining the positioning of first and second members relative to one another as claimed in claim 1 wherein the step of generating a plurality of distinct electromagnetic signals comprises generating signals at two points on a first axis passing through said central position, said two points on said first axis being equally spaced from and on opposite sides of said central position, and generating signals at two points on a second axis crossing said first axis substantially at said central position, said two points on said second axis being equally spaced from and on opposite sides of said central position, the signals received from said two points on said first axis being combined with the signals received from said two points on said second axis to determine the positioning of said first and second members in said first and second directions.

5. In a web measuring system, a method for determining the positioning of first and second members relative to one another as claimed in claim 1 wherein the step of generating a plurality of distinct electromagnetic signals comprises generating signals at first and second points on a first axis passing through said central position, said first and second points being equally spaced from and on opposite sides of said central position, and generating signals at third and fourth points on a second axis crossing said first axis substantially at said central position, said third and fourth points being equally spaced from and on opposite sides of said central position, said points being arranged relative to one another such that when viewed from said second side of said web of material said points are arranged in clockwise order from point one to point three to point two to point four, the signals received from said first and second points being combined with the signals received from said third and fourth points to determine the positioning of said first and second members in said first and second directions.

6. In a web measuring system, a method for determining the positioning of first and second members relative to one another as claimed in claim 5 wherein said first axis is oriented at approximately 45° relative to said first direction and said second axis is oriented at approximately 135° relative to said first direction, the signals received from said first and third points being subtracted from the signals received from said second and fourth points to determine relative positioning between said first and second members in said first direction.

7. In a web measuring system, a method for determining the positioning of first and second members relative to one another as claimed in claim 5 wherein said first axis is oriented at second axis is oriented at approximately 135° relative to said first direction, the signals received from said second and third points being subtracted from the signals received from said first and fourth points to determine relative positioning between said first and second members in said second direction.

8. In a web measuring system, a method for determining the positioning of first and second members relative to one another as claimed in claim 5 wherein said first axis is oriented at approximately 45° relative to said first direction and said second axis is oriented at approximately 135° relative to said first direction, the signals received from said second point being subtracted from the signals received from said first point to determine relative positioning between said first and second members along said first axis, and the signals received from said third point being subtracted from the signals received from said fourth point to determine relative positioning between said first and second members along said second axis.

9. In a web measuring system, a method for determining the positioning of first and second members relative to one another as claimed in claim 5 wherein said first axis is oriented at approximately 45° relative to said first direction and said second axis is oriented at approximately 135° relative to said first direction, the signals received from said first and third points being subtracted from the signals received from said second and fourth points to determine relative positioning between said first and second members in said first direction, and the signals received from said second and third points being subtracted from the signals received from said first and fourth points to determine relative positioning between said first and second members in said second direction.

10. In a web measuring system, a method for determining the positioning of first and second members relative to one another as claimed in claim 9 wherein the signals received from said second point are subtracted from the signals received from said first point to determine relative positioning between said first and second members along said first axis, and the signals received from said third point are subtracted from the signals received from said fourth point to determine relative positioning between said first and second members along said second axis.

11. In a web measuring system, a method for determining the positioning of first and second members relative to one another as claimed in claim 1 wherein the step of generating a plurality of distinct electromagnetic signals comprises generating signals at first and second points on a first axis passing through said central position, said first and second points being equally spaced from and on opposite sides of said central position, and generating signals at third and fourth points on a second axis crossing said first axis substantially at said central position, said third and fourth points being equally spaced from and on opposite sides of said central position, said points being arranged relative to one another such that when viewed from said second side of said web of material said points are arranged in clockwise order from point one to point four to point two to point three, the signals received from said first and second points being combined with the signals received from said third and fourth points to determine the positioning of said first and second members in said first and second directions.

12. In a system for measuring characteristics of a web of sheet material moving in a first direction by reciprocally scanning sensor means across said web in a second direction substantially perpendicular to said first direction, said sensor means including first and second members positioned on opposite sides of said web and being moved relative to one another as a result of said sensor means being scanned across said web, apparatus for determining the positioning of said first and second members relative to one another comprising:

a plurality of electromagnetic energy transmitters associated with said first member on a first side of said web of material and surrounding a central position, said transmitters each transmitting a different frequency electromagnetic energy signal;

an electromagnetic energy sensor associated with said second member on a second side of said web and substantially directly opposite to said central position for receiving signals transmitted by said transmitters; and circuit means connected to said sensor for receiving and combining signals transmitted by said plurality of transmitters to determine the positioning between said first and second members.

13. In a web measuring system, apparatus for determining the positioning of first and second members relative to one another as claimed in claim 12 wherein said circuit means includes means for algebraically summing said plurality of signals to determine the separation between said first and second members.

14. In a web measuring system, apparatus for determining the positioning of first and second members relative to one another as claimed in claim 12 wherein said plurality of electromagnetic energy transmitters comprises first and second transmitters positioned on a first axis passing through said central position, said first and second transmitters being equally spaced from and on opposite sides of said central position, and third and fourth transmitters positioned on a second axis crossing said first axis substantially at said central position, said third and fourth transmitters being equally spaced from and on opposite sides of said central position, said transmitters being arranged relative to one another such that when viewed from said second side of said web of material said transmitters are arranged in clockwise order from said first transmitters to said third transmitter to said second transmitter to said fourth transmitter, said circuit means combining the signals received from said first and second transmitters with the signals received from said third and fourth transmitters to determine the positioning of said first and second members in said first and second directions.

15. In a web measuring system, apparatus for determining the positioning of first and second members relative to one another as claimed in claim 19 wherein said first axis is oriented at approximately 45° relative to said first direction and said second axis is oriented at approximately 135° relative to said first direction, said circuit means combining the signals received from said transmitters by subtracting the signals received from said first and third transmitters from the signals received from said second and fourth transmitters to determine relative positioning between said first and second members in said first direction.

16. In a web measuring system, apparatus for determining the positioning of first and second members relative to one another as claimed in claim 14 wherein said first axis is oriented at approximately 45° relative to said first direction and said second axis is oriented at approximately 135° relative to said first direction, said circuit means combining the signals received from said transmitters by subtracting the signals received from said second and third transmitters from the signals received from said first and fourth transmitters to determine relative positioning between said first and second members in said second direction.

17. In a web measuring system, apparatus for determining the positioning of first and second members relative to one another as claimed in claim 14 wherein said first axis is oriented at approximately 45° relative to said first direction and said second axis is oriented at approximately 135° relative to said first direction, said circuit means combining the signals received from said transmitters by subtracting the signals received from said first and third transmitters from the signals received from said second and fourth transmitters to determine relative positioning between said first and second members in said first direction, and combining the signals received from said transmitters by subtracting the signals received from said second and third transmitters from the signals received from said first and fourth transmitters to determine relative positioning between said first and second members in said second direction.

18. In a web measuring system, apparatus for determining the positioning of first and second members relative to one another as claimed in claim 14 wherein said first axis is oriented at approximately 45° relative to said first direction and said second axis is oriented at approximately 135° relative to said first direction, said circuit means combining the signals received from said transmitters by subtracting the signals received from said second transmitter from the signals received from said first transmitter to determine relative positioning between said first and second members along said first axis, and by subtracting the signals received from said third transmitter from the signals received from said fourth transmitter to determine relative positioning between said first and second members along said second axis.

19. In a web measuring system, apparatus for determining the positioning of first and second members relative to one another as claimed in claim 12 wherein said plurality of electromagnetic energy transmitters comprises first and second transmitters positioned on a first axis passing through said central position, said first and second transmitters being equally spaced from and on opposite sides of said central position, and third and fourth transmitters positioned on a second axis crossing said first axis substantially at said central position, said third and fourth transmitters being equally spaced from and on opposite sides of said central position, said transmitters being arranged relative to one another such that when viewed from said second side of said web of material said transmitters are arranged in clockwise order from said first transmitter to said fourth transmitter to said second transmitter to said third transmitter, said circuit means combining the signals received from said first and second transmitters with the signals received from said third and fourth transmitters to determine the positioning of said first and second members in said first and second directions.

* * * * *

UNITED STATES PATENT AND TRADEMARK OFFICE
CERTIFICATE OF CORRECTION

PATENT NO. : 5,117,686
DATED : June 2, 1992
INVENTOR(S) : Ralph S. Lorenz It is certified that error appears in the above-identified patent and that said Letters Patent is hereby corrected as shown below:

Col. 10, line 17, "oriented at second" should read --oriented at approximately 45° relative to said first direction and said second--.

Col. 11, line 62, "first transmitters" should read --first transmitter--.

Col. 12, line 3, "claim 19" should read --claim 14--.

Signed and Sealed this

Tenth Day of August, 1993

Attest:

MICHAEL K. KIRK

*Attesting Officer*    Acting Commissioner of Patents and Trademarks